United States Patent [19]

Obara et al.

[11] Patent Number: 5,519,160

[45] Date of Patent: May 21, 1996

[54] ALKYL 3-(SUBSTITUTED OR UNSUBSTITUTED BENZYLIDENE)-1-ALKYL-2-OXOCYCLOPENTANECARBOXYLATE DERIVATIVES, PROCESS FOR PREPARING THE SAME

[75] Inventors: Heitaro Obara, Sendai; Satoru Kumazawa, Iwaki, both of Japan

[73] Assignee: Kureha Chemical Industry Co., Ltd., Tokyo, Japan

[21] Appl. No.: 340,150

[22] Filed: Nov. 15, 1994

[51] Int. Cl.⁶ .................................................. C07L 69/76
[52] U.S. Cl. ........................... 560/51; 568/379; 568/348; 568/356
[58] Field of Search ...................... 560/51; 568/379, 568/348, 356

[56] References Cited

U.S. PATENT DOCUMENTS

| | | |
|---|---|---|
| 4,496,766 | 1/1985 | Tsuji et al. . |
| 4,575,570 | 3/1986 | Kataoka et al. . |
| 4,863,505 | 9/1989 | Kumazawa et al. . |
| 4,938,792 | 7/1990 | Kumazawa et al. . |
| 5,162,356 | 11/1992 | Arahira et al. . |
| 5,256,683 | 10/1993 | Hutt et al. . |
| 5,258,404 | 11/1993 | Ichinose et al. . |

FOREIGN PATENT DOCUMENTS

0537909A1  4/1993  European Pat. Off. ...... C07C 69/757

OTHER PUBLICATIONS

Heinrich Hellmann, et al Justus Liebigs Annalen Der Chemie 656, 89–96C(1962).
Chemical Abstracts 57:14951 (1962).

*Primary Examiner*—Paul J. Killos
*Attorney, Agent, or Firm*—Testa, Hurwitz & Thibeault

[57] ABSTRACT

Derivatives of alkyl 3-(substituted or unsubstituted benzylidene)-1-alkyl-2-oxocylopentanecarboxylate of the following formula (I),

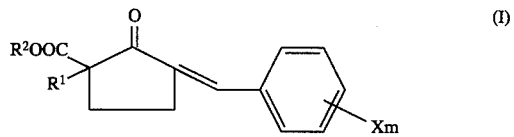

wherein $R^1$ and $R^2$ individually represent a lower alkyl group; X is a halogen atom, a cyano group, an alkyl group, a haloalkyl group, a phenyl group, or a nitro group; and m is an integer of 0 to 5; provided when m is 2 or larger, Xs may be either the same or different. The compounds are useful themselves as an effective ingredient of antifungal compositions, and can be used for intermediates of agriculture chemicals and medicines.

6 Claims, No Drawings

ALKYL 3-(SUBSTITUTED OR UNSUBSTITUTED BENZYLIDENE)-1-ALKYL-2-OXOCYCLOPENTANECARBOXYLATE DERIVATIVES, PROCESS FOR PREPARING THE SAME

BACKGROUND OF THE INVENTION

1. Field of the Invention

The present invention relates to a derivative of alkyl 3-(substituted or unsubstituted benzylidene)-1-alkyl-2-oxo-cyclopentanecarboxylate, a process for preparing this compound, an antifungal composition comprising the same, and use of this compound as an intermediate for the preparation of an antifungal compound.

2. Description of Background Art

Derivatives of 2-(substituted or unsubstituted benzyl)-5-alkylcyclopentanone are described as intermediates for the manufacture of agriculture chemicals, medicines, and the like in U.S. Pat. Nos. 4,863,505, 4,938,792, and U.S. Pat. No. 5,162,356.

An improved manufacturing process of these intermediate compounds is proposed in U.S. Pat. No. 5,258,404.

Further, derivatives of 2-(substituted or unsubstituted benzylidene)-5-alkylcyclopentanone are described as intermediates of agriculture chemicals in U.S. Pat. No. 5,256,683.

The present inventors have conducted studies on a novel process for preparing derivatives of 2-(substituted or unsubstituted benzyidene)-5-alkylcyclopentanone or derivatives of 2-(substituted or unsubstituted benzyl)-5-alkylcyclopentanone, both useful as intermediates for the manufacture of valuable compounds as mentioned above, and found that either intermediate compound can be produced from derivatives of alkyl 3-(substituted or unsubstituted benzylidene)-1-alkyl-2-oxocyclopentanecarboxylate, which are novel compounds, and these novel compounds are useful as an effective ingredient of an antifungal composition. These findings have led to the completion of the present invention.

The present inventors have found that derivatives of alkyl 3-(substituted or unsubstituted benzylidene)-1-alkyl-2-oxo-cylopentanecarboxylate of the following formula (I),

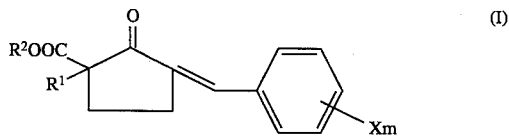

wherein $R^1$ and $R^2$ individually represent a lower alkyl group; X is a halogen atom, a cyano group, an alkyl group, a haloalkyl group, a phenyl group, or a nitro group; and m is an integer of 0 to 5; provided when m is 2 or larger, Xs may be either the same or different, are compounds which can be converted into either derivatives of 2-(substituted or unsubstituted benzylidene)-5-alkylcyclopentanone the following formula (VIb) or derivatives of 2-(substituted or unsubstituted benzyl)-5-alkylcyclopentanone the following formula (VIIb),

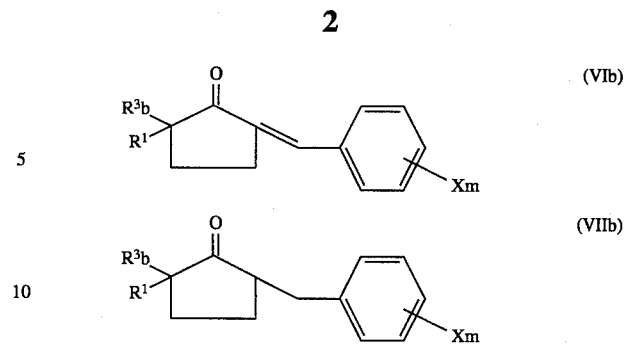

wherein $R^1$, X and m are the same as defined above, and $R^3b$ represents a hydrogen atom or a lower alkyl group.

SUMMARY OF THE INVENTION

Accordingly, an object of the present invention is to provide a derivative of alkyl 3-(substituted or unsubstituted benzylidene)-1-alkyl-2-oxocylopentanecarboxylate of the following formula (I),

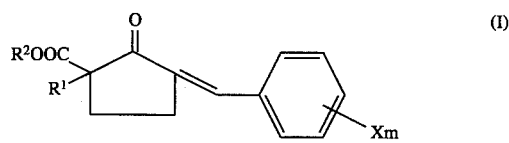

wherein $R^1$ and $R^2$ individually represent a lower alkyl group; X is a halogen atom, a cyano group, an alkyl group, a haloalkyl group, a phenyl group, or a nitro group; and m is an integer of 0 to 5; provided when m is 2 or larger, Xs may be either the same or different.

Another object of the present invention is to provide a process for preparing a derivative of alkyl 3-(substituted or unsubstituted benzylidene)-1-alkyl-2-oxocylopentanecarboxylate of formula (I), which comprises reacting a derivative of alkyl 1-alkyl-2-oxocylopentanecarboxylate of formula (II) and a substituted or unsubstituted benzaldehyde of formula (III) under basic conditions according to the following reaction formula,

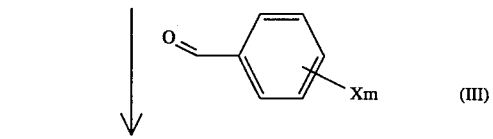

wherein $R^1$, $R^2$, X and m are the same as defined above.

Still another object of the present invention is to provide a process for preparing a derivative of 2-(substituted or unsubstituted benzylidene)-5-alkylcyclopentanone of formula (IV) which comprises hydrolyzing and decarboxylating a derivative of alkyl 3-(substituted or unsubstituted benzylidene)-1-alkyl-2-oxocylopentanecarboxylate of formula (I), according to the following reaction formula,

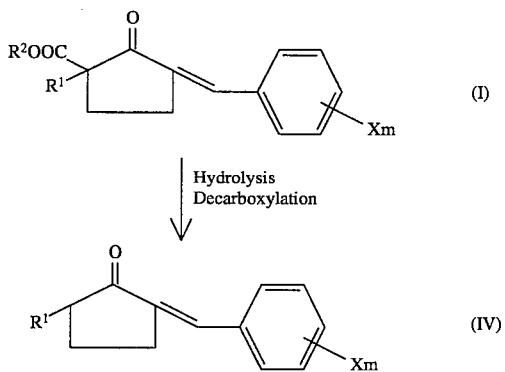

wherein $R^1$, $R^2$, X and m are the same as defined above

A further object of the present invention is to provide a process for preparing a derivative of 2-(substituted or unsubstituted benzylidene)-5,5-dialkylcyclopentanone of formula (VI) which comprises alkylating a derivative of 2-(substituted or unsubstituted benzylidene)-5-alkylcylopentanone of formula (IV) with an halogenated alkyl compound (V) under basic conditions, according to the following reaction formula,

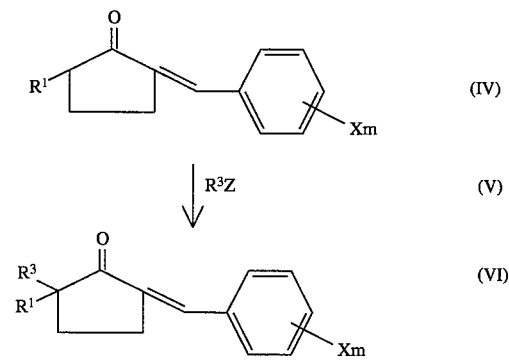

wherein $R^1$, X and m are the same as defined above, $R^3$ is a lower alkyl group, and Z indicates a halogen atom.

A still further object of the present invention is to provide a process for preparing a derivative of 2-(substituted or unsubstituted benzyl)-5-alkylcyclopentanone of formula (VIIb) which comprises reducing a derivative of 2-(substituted or unsubstituted benzylidene)-5-alkylcyclopentanone of formula (VIb), according to the following reaction formula,

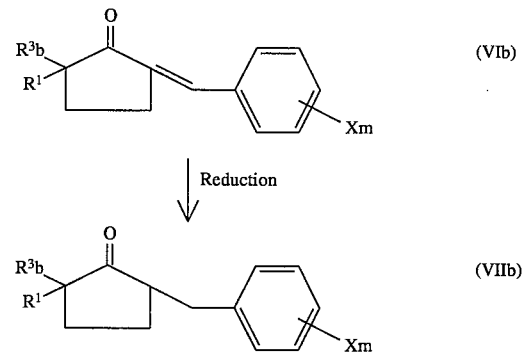

wherein $R^1$, X and m are the same as defined above, $R^3b$ is a hydrogen atom or a lower alkyl group.

It is still another object of the present invention to provide an antifungal composition comprising a derivative of alkyl 3-(substituted or unsubstituted benzylidene)-1-alkyl-2-oxo-cylopentanecarboxylate of the following formula (I),

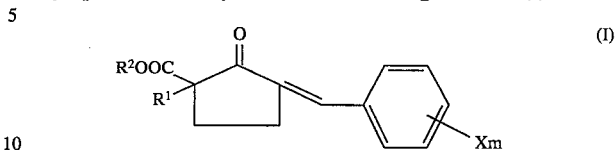

wherein $R^1$, $R^2$, X and m are the same as defined above, as an effective ingredient.

Other objects, features and advantages of the invention will hereinafter become more readily apparent from the following description.

DETAILED DESCRIPTION OF THE INVENTION AND PREFERRED EMBODIMENTS

The compounds I-1 and I-2 in the following Table 1 are given as specific examples of the derivative of alkyl 3-(substituted or unsubstituted benzylidene)-1-alkyl-2-oxocylopentanecarboxylate.

TABLE 1

| Compound No. | Substituent groups in formula (I) | | |
|---|---|---|---|
| | $R^1$ | $R^2$ | Xm |
| I-1 | $CH_3$ | $CH_3$ | 4-Cl |
| I-2 | $CH_3CH(CH_3)$ | $CH_3$ | 4-Cl |

In the above Table 4-Cl indicates that the 4-position is substituted by a chlorine atom.

The following diluents, given as examples, are used in various reactions of the present invention. Lower aliphatic acids, such as acetic acid and propionic acid; hydrocarbons, such as benzene, toluene, xylene, and hexane; halogenated hydrocarbons, such as methylene chloride, chloroform, and carbon tetrachloride; alcohols, such as methanol, ethanol, isopropanol, and t-butanol; ethers, such as diethyl ether, dimethoxyethane, di-isopropyl ether, tetrahydrofuran, and dioxane; and other diluents, such as acetonitrile, acetone, methylformamide, dimethylformamide, dimethylacetamide, N-methyl-pyrrolidone, dimethylsulfoxide, and the like.

In addition of these diluents, the reactions may be carried out in the presence of a base or an acid.

The following compound are given as examples of the bases.

Alkali metal carbonates, such as sodium carbonate and potassium carbonate; alkali metal hydroxides, such as sodium hydroxide and potassium hydroxide; alkali metal alkoxides, such as sodium methoxide, sodium ethoxide, and potassium t-butoxide; alkali metal hydrides, such as sodium hydride and potassium hydride, organic alkali metal compounds, such as n-butyl lithium; and organic tert-amine compounds, such as triethylamine and prydine.

Given as examples of the acids used in the reactions are inorganic acids, such as hydrochloric acid, hydrobromic acid, hydriodic acid, and sulfuric acid; and organic acids, such as formic acid, acetic acid, butyric acid, and p-toluenesulfonic acid.

Hydrogenation catalysts which can be used include platinum, palladium, nickel and the like with an increased surface area for promoting the activity, and these metals carried on carbons such as activated carbon or supported by alumina.

Compound (I) can be obtained by the benzylidation of the derivative of alkyl 1-alkyl-2-oxocylopentane-carboxylate (II) by a substituted or unsubstituted benzaldehyde (III).

Specifically, the compound (I) can be prepared by the aldol condensation reaction of compound (II) and compound (III) in a lower alcohol, preferably in a mixed solvent of methanol and water, using an alkali metal hydroxide, such as sodium hydroxide or potassium hydroxide, as a catalyst. The compound (I) can be produced almost quantitatively by reacting at room temperature to about 40° C. for about 2–10 hours.

Examples of compound (III) which can be used for the reaction include benzaldehyde, 4-cyanobenzaldehyde, 4-chlorobenzaldehyde, 4-fluorobenzaldehyde, 4-bromobenzaldehyde, 2,4-dichlorobenzaldehyde, 3,4-dichlorobenzaldehyde, 2-chloro-4-fluorobenzaldehyde, 3,4-difluorobenzaldehyde, 2,6-difluorobenzaldehyde, p-tolualdehyde, 4-(t-butyl)benzaldehyde, 4-phenylbenz-aldehyde, 4-(trifluoromethyl)benzaldehyde, 4-nitrobenzaldehyde, and pentafluorobenzaldehyde, and the like.

In compound (I), $R^1$ and $R^2$ individually represent a lower alkyl group. Preferred lower alkyl groups are methyl, ethyl and isopropyl.

X represents a halogen atom, a cyano group, an alkyl group, a haloalkyl group, a phenyl group, or a nitro group. Preferred groups for X are chlorine, fluorine, bromine, phenyl, and $C_1$–$C_4$ alkyl, with more preferred groups being methyl, tert-butyl, and $C_1$–$C_4$ haloalkyl, and particularly preferred being trifluoromethyl.

The haloalkyl represented by X are groups in which one or more hydrogen atoms in alkyl groups are substituted by halogen atoms.

m is an integer of 0 to 5, and preferably 0–2.

A derivative of 2-(substituted or unsubstituted benzylidene)-5-alkylcylopentanone (IV) can be obtained easily at a high yield by the hydrolysis and decarboxylation of compound (I) thus produced.

The hydrolysis and decarboxylation reactions can be carried out either basic or acidic conditions.

When the reactions are carried out under basic conditions, the use of lower alcohols or aromatic hydrocarbons together with water is preferred. Sodium hydroxide or potassium hydroxide is preferably used as the base. The reaction temperature is from 40° C. to the refluxing temperature, preferably from 70° C. to the refluxing temperature.

When the reactions are carried out under acidic conditions, the use of acetic acid together with water, as a solvent, is preferred. An inorganic acid such as hydrochloric acid or hydrobromic acid is used as a catalyst. The reaction temperature is from 50° C. to the refluxing temperature, preferably from 80° C. to the refluxing temperature.

For obtaining a derivative of 2-(substituted or unsubstituted benzylidene)-5,5-dialkylcyclopentanone of formula (VI), the derivative of 2-(substituted or unsubstituted benzylidene)-5-alkylcylopentanone of formula (IV) is alkylated using alkyl halogen compound (V) under basic conditions.

The alkylation reaction is carried out preferably using one or more aprotic polar solvents such as, for example, nitril-type solvents, e.g. acetonitrile; amide-type solvents, e.g. methylformamide, dimethylformamide, dimethylacetamide, N-methylpyrrolidone; and sulfur-containing solvents, e.g. dimethylsulfoxide.

Alkyl metal hydrides and alkaline metal hydrides can be given as examples of the base, with especially preferable bese being sodium hydride.

The reaction temperature is 50°–100° C., and preferably 60°–90° C. Because the raw materials are consumed in about 0.5–10 hours, the reaction is carried out for approximately this time period.

Methyl bromide, methyl iodide, ethyl iodide, propyl bromide, isopropyl iodide, n-butyl chloride, or the like is used as the alkyl halogen compound (V). When no iodide compound is used as the alkyl halogen compound (V), it is desirable to use a catalytic amount of an alkali metal iodide.

A derivative of 2-(substituted or unsubstituted benzyl)-5-alkylcyclopentanone of formula (VIIb) is obtained by reducing a derivative of 2-(substituted or unsubstituted benzylidene)-5-alkylcyclopentanone of formula (VIb), wherein the double bond of compound of formula (VIb) is hydrogenated using palladium-carbon, preferably, in ethanol.

The compound (VIIb) can be obtained at a high yield by carrying out the hydrogenation reaction at a temperature of from room temperature to about 40° C. under atmospheric pressure or under pressure, preferably under atmospheric pressure, by absorbing a theoretical quantity of hydrogen.

Isolation of the compounds (I), (IV), (VI), (VIb), and (VIIb) prepared by the above processes can be carried out by a suitable combination of conventional chemical separation methods, such as column chromatography, recrystallization, distillation, or the like, or by a suitable combination of these methods.

The derivative of alkyl 3-(substituted or unsubstituted benzylidene)-1-alkyl-2-oxocylopentane-carboxylate (I) of the present invention is useful itself as an effective ingredient of antifungal compositions. In addition, it can be used for intermediates of agriculture chemicals and medicines.

When the derivative of alkyl 3-(substituted or unsubstituted benzylidene)-1-alkyl-2-oxocylopentane-carboxylate of formula (I) is used as an antifungal agent, it is usually made into a formulation, together with adjuvants, in the form of powder, wettable or water-dispersible powder, granule, emulsion concentrate, or the like, although the compound may be used alone.

Such a formulation may contain one or more compounds (I) of the present invention in an amount of 0.1 to 95%, preferably 0.5 to 90%, and more preferably 2 to 70% by weight.

Examples of carriers, diluents, surfactants, and the like which can be used as adjuvants in the composition of the present invention are as follows. Talc, kaolin, bentonite, diatomaceous earth, white carbon, clay, and the like, can be used as solid carriers; and water, xylene, toluene, chlorobenzene, cyclohexane, cyclohexanone, dimethylsulfoxide, dimethylformamide, N-methylpyrrolidone, alcohol, and the like are used as liquid diluents. Different types of surfactants may be used depending on the effects intended; e.g., polyoxyethylene alkylaryl ether, polyoxyethylene sorbitan monolaurate, etc., as emulsifier; lignin sulfonate, dibutylnaphthalene sulfonate, etc., as dispersant; alkyl sulfonate, alkylphenyl sulfonate, etc., as wetting agents.

Depending on the types the formulations are used directly or after having been diluted to a prescribed concentration by diluents such as water. When the formulation is used after dilution, its concentration is preferably in the range of 0.001 to 1.0%. The compound of the present invention may be applied to fields, orchards, greenhouses, etc., in an amount of 20 to 5,000 g, preferably 50 to 1,000 g, per 1 hector. The concentrations and amounts of use may be varied depending on types of the preparation, the time at which it is applied, the manner and the site in which it is used, and the plant to which it is applied. Thus, the amount and concentration may be increased or decreased without regard to the above specified ranges.

In addition, the compound of the present invention can be used in combination with other effective ingredients such as, for example, antifungals, antibacterials, insecticides, acaricides, or herbicides.

Other features of the invention will become apparent in the course of the following description of the preparation examples and reference examples of the derivatives of alkyl 3-(substituted or unsubstituted benzylidene)-1-alkyl-2-oxo-cylopentanecarboxylate (I), formulation examples, and test examples. It is understood that these are given for illustration of the invention and are not intended to be limiting thereof.

EXAMPLES

Preparation Examples

Preparation Example 1

Preparation of methyl 3-(4-chlorobenzylidene)-1-methyl-2-oxocylopentanecarboxylate (I-1)

To a solution of 3.4 g of sodium hydroxide in 770 ml of water were added 15 g of methyl 1-methyl-2-oxocylopentanecarboxylate (prepared in Reference Example 1 hereinafter) and a solution of 13.5 g of 4-chlorobenzaldehyde in 800 ml of methanol, and the mixture was stirred for 5 hours at room temperature. The reaction mixture was neutralized with diluted hydrochloric acid and the solvent was evaporated under reduced pressure. The residue was extracted with ethyl acetate. The organic layer was washed with water and dried. Ethyl acetate was evaporated under reduced pressure to obtain 25 g of an oily matter.

Yield, 93.4%

MS (m/z): 278(M$^+$)

Preparation Example 2

Preparation of methyl 3-(4-chlorobenzylidene)-1-(isopropyl)-2-oxocylopentanecarboxylate To a solution of 4 g of sodium hydroxide in 1000 ml of water were added 21 g of methyl 1-isopropyl-2-oxocylopentanecarboxylate (prepared in Reference Example 2 hereinafter) and a solution of 16 g of 4-chlorobenzaldehyde in 1000 ml of methanol, and the mixture was stirred for 5 hours at room temperature. The reaction mixture was neutralized with diluted hydrochloric acid and the precipitate was collected by filtration. Product 33.6 g (yield, 96.2%)

m.p 93°–94° C. (recrystallized from methanol)

MS (m/z): 307(M$^+$)

NMR (CDCl$_3$, δ): 0.85(d, 3H, J=6 Hz), 0.95(d, 3H, J=6 Hz), 1.70–3.20(m, 5H), 3.74(s, 3H), 7.27(bs, 1H), 7.42(bs, 4H)

Preparation Example 3

Preparation of 2-(4-chlorobenzylidene)-5-methylcylopentanone

A solution of 12 g of sodium hydroxide in 20 ml of water was added to 10 g of methyl 3-(4-chloro-benzylidene)-1-methyl-2-oxocylopentanecarboxylate (I-1) (prepared in Example 1). The mixture was stirred for 2 hours at 80° C. The reaction mixture was poured into 10% aqueous solution of hydrochloric acid and extracted with ethyl acetate. The organic layer was washed with water and dried over anhydrous sodium sulfate. The solvent was evaporated to obtain 4.1 g of an oily matter (yield, 51.8%).

Preparation Example 4

Preparation of 2-(4-chlorobenzylidene)-5-isopropylcylopentanone

To a mixed solution of 150 ml of toluene, 50 ml of isopropanol, and 100 ml of water were added 58.6 g of sodium hydroxide and 50 g of methyl 3-(4-chlorobenzylidene)-1-isopropyl-2-oxocylopentanecarboxylate (prepared in Example 2). The mixture was stirred for 4 hours at 70°–80° C. The reaction mixture was poured into 2000 ml of 10% aqueous solution of hydrochloric acid and extracted with 300 ml of ethyl acetate. The organic layer was washed with water and dried, followed by evaporation of the solvent to obtain the target compound.

m.p. 80°–81° C. (recrystallized from methanol)

MS (m/z): 249(M$^+$)

NMR (CDCl$_3$, δ): 0.85(d, 3H, J=6 Hz), 1.04(d, 3H, J=6 Hz), 1.20–3.10(m, 6H), 7.30(t, 1H, J=2 Hz), 7.42(bs, 4H)

Preparation Example 5

Preparation of 2-(4-chlorobenzylidene)-5,5-dimethylcylopentanone 2.4 g of sodium hydride (60% oily sodium hydride washed with anhydrous benzene) was added to 100 ml of anhydrous dimethylformamide under nitrogen atmosphere while stirring. 24 g of 2-(4-chlorobenzylidene)-5-methylcylopentanone (prepared in Example 3) was added to the mixture, followed by stirring at room temperature until generation of hydrogen was terminated. After the addition of 15 g of methyl iodide, the mixture was stirred for a further 2 hours at 60° C. The reaction mixture thus obtained was allowed to cool, poured into ice water, and extracted with ethyl acetate. The organic layer was washed with water and dried over anhydrous sodium sulfate, followed by evaporation of the solvent under reduced pressure. The residue was solidified with the addition of a small amount of hexane to obtain the title compound.

Product 22.0 g (yield, 86.2%)

m.p. 118°–120° C.

Preparation Example 6

Preparation of 2-(4-chlorobenzyl)-5,5-dimethylcylopentanone 5 g of 2-(4-chlorobenzylidene)-5,5-dimethylcylopentanone (prepared in Example 5) was dissolved in 40 ml of ethanol, and 60 mg palladium-carbon (10%) was added to the mixture. The hydrogenation reaction was carried out under normal pressure until theoretical amount of hydrogen was absorbed.

Palladium-carbon was removed from the reaction mixture by filtration. Ethanol was evaporated from the filtrate under reduced pressure, to obtain a colorless oily matter as the residue. This colorless oily matter was purified by silica gel column chromatography, thus obtaining the title compound as an oil.

Product 4.2 g (yield, 83.3%)

Preparation Example 7

Preparation of 2-(4-chlorobenzyl)-5-isopropylcylopentanone 1.0 g of 2-(4-chlorobenzylidene)-5-isopropylcylopentanone (prepared in Example 4) was dissolved in 10 ml of ethanol, and 20 mg palladium-carbon (10%) was added to the solution. The hydrogenation reaction was carried out under normal pressure until theoretical amount of hydrogen was absorbed.

Palladium-carbon was removed from the reaction mixture by filtration. Ethanol was evaporated from the filtrate under reduced pressure, to obtain a colorless oily matter as the residue. This colorless oily matter was purified by silica gel column chromatography, thus obtaining 0.85 g (yield, 84.3%) of the title compound as an oil.

REFERENCE EXAMPLES

Reference Example 1

Preparation of methyl 1-methyl-2-oxocylopentanecarboxylate 2.52 g of sodium hydride (60% oily sodium hydride washed with anhydrous benzene) was added to 50 ml of anhydrous dimethylformamide under nitrogen atmosphere while stirring. 14.2 g of 2-methoxycarbonylcylopentanone was added to the mixture, followed by stirring at room temperature until generation of hydrogen was terminated. Next, 15 g of methyl iodide was added, and the mixture was stirred for a further 2 hours at 60° C. The reaction mixture thus obtained was poured into 300 ml of diluted hydrochloric acid solution and extracted with ethyl acetate. The organic layer was washed with water and dried over anhydrous sodium sulfate, followed by evaporation of the solvent under reduced pressure. The oily residue obtained was purified by vacuum distillation to obtain 14.5 g of the title compound.

b.p. 100° C./1 mm Hg

Reference Example 2

Preparation of methyl 1-isopropyl-2-oxocylopentanecarboxylate 7.7 g of sodium hydride (free of oil) was added to 80 ml of dimethylformamide. 25 g of 2-methoxycarbonylcylopentanone was slowly added dropwise while cooling with ice. The reaction mixture was allowed to come to room temperature, whereupon 45 g of isopropyl iodide was added, followed by stirring for a further 3.5 hours at 70°–80° C. The reaction mixture thus obtained was poured into 400 ml of 10% hydrochloric acid solution and extracted with 100 ml of ethyl acetate. The organic layer was washed with water, dried, and concentrated to obtain 25.5 g (yield, 78.7%) of the title compound.

MS (m/z): 184($M^+$)

NMR ($CDCl_3$, δ): 0.80(d, 3H, J=6 Hz), 0.85(d, 3H, J=6 Hz), 1.10–2.10(m, 7H), 3.68(s, 3H)

FORMULATION EXAMPLES

Formulations containing the derivatives of alkyl 3-(substituted or unsubstituted benzylidene)-1-alkyl-2oxocylopentanecarboxylate (I) as an effective ingredient

Formulation Example 1 <Dust>

| | parts by weight |
|---|---|
| Compound (I-1) | 3 |
| Clay | 40 |
| Talc | 57 |

The above ingredients were pulverized and mixed to obtain a dust.

Formulation Example 2 <wettable Powder>

| | parts by weight |
|---|---|
| Compound (I-2) | 50 |
| Lignin sulfonate | 5 |
| Alkyl sulfonate | 3 |
| Diatomaceous earth | 42 |

The above ingredients were pulverized and mixed to obtain wettable powder.

Formulation Example 3 <Granules>

| | parts by weight |
|---|---|
| Compound (I-2) | 5 |
| Bentonite | 43 |
| Clay | 45 |
| Lignin sulfonate | 7 |

The above ingredients were mixed and kneaded with the addition of water. The mixture was extruded and then dried to obtain granules.

Formulation Example 4 <Emulsion Concentrate>

| | parts by weight |
|---|---|
| Compound (I-1) | 20 |
| Polyoxyethylene alkylaryl ether | 10 |
| Polyoxyethylenesorbitan monolaurate | 3 |
| Xylene | 67 |

The above ingredients were mixed and dissolved to obtain an emulsion concentrate.

TEST EXAMPLE

<Test for controlling effects against various fungi>

A test for identifying the effects of compound (I-1) and compound (I-2) of the present invention on controlling various fungi causing plant diseases was carried out.

(1) Test method

The compounds of the present invention (compound (I-1) and compound (I-2)) were dissolved in dimethylsulfoxide to make solutions with a prescribed concentration. 0.6 ml of each solution and 60 ml PAS medium at about 60° C. were mixed thoroughly in a 100 ml conical flask, charged in a Petri dish, and solidified.

Test fungi were cultured in advance in plate media. Plates were punched with a 4 mm cork borer and the fungi were inoculated to plate media containing test compounds. After inoculation fungi were cultured at their optimal growth temperature for 1–3 days, and the mycerial tuft diameter of each fungus was measured. The diameter was compared with the corresponding diameter of the mycerial tuft grown in a medium with no addition of the test compound. The mycerium growth controlling rate was determined according to the following formula.

R=100(dc-dt)/dc wherein R is the mycerium growth controlling rate (%), dc is the mycerial tuft diameter in the untreated medium, and dt is the mycerial tuft diameter in the medium treated with the test compound.
(2) Test results The results are shown in Table 2, wherein R was classified according to the following criteria.

0: R is smaller than 40%.
1: R is 40–80%.
2: R is larger than 80%.

TABLE 2

| Compound No. | Concentration of test compound (μg/ml) | Tested fungi | | |
|---|---|---|---|---|
| | | H.s. | R.s. | S.c. |
| I-1 | 100 | 1 | 1 | 1 |
| I-2 | 100 | 1 | 1 | 2 |

In Table 2, symbols are abbreviations of the following tested fungi.

H.s.: *Helminthosporium sigmoideum*
R.s.: *Rhizoctonia solani*
S.c.: *Sclerotinia sclerotiorum*

Obviously, numerous modifications and variations of the present invention are possible in light of the above teachings. It is therefore to be understood that within the scope of the appended claims, the invention may be practiced otherwise than as specifically described herein.

What is claimed is:

1. A compound of the formula

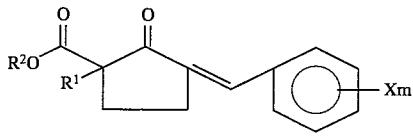

wherein $R^1$ and $R^2$ individually represent a lower alkyl group; X is a halogen atom, a cyano group, an alkyl group, a haloalkyl group, or a phenyl group; and m is an integer of 0 to 5; provided that when m is 2 or larger, Xs may be either the same of different.

2. A process for preparing the compound of claim 1, which comprises reacting a compound of the formula

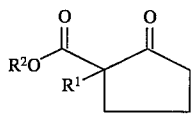

and a compound of the formula

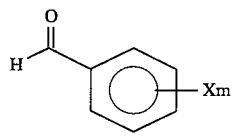

under basic conditions wherein $R^1$ and $R^2$ individually represent a lower alkyl group; X is a halogen atom, a cyano group, an alkyl group, a haloalkyl group, or a phenyl group; and m is an integer of 0 to 5; provided that when m is 2 or larger, Xs may be either the same or different.

3. A process for preparing a compound of the formula

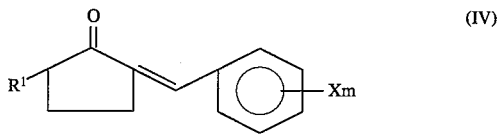

which comprises hydrolyzing and decarboxylating a compound of formula (I) wherein $R^1$ and $R^2$ individually represent a lower alkyl group; X is a halogen atom, a cyano group, an alkyl group, a haloalkyl group, a phenyl group, or a nitro group; and m is an integer of 0 to 5; provided that when m is 2 or larger, Xs may be either the same or different.

4. A process for preparing a compound of the formula

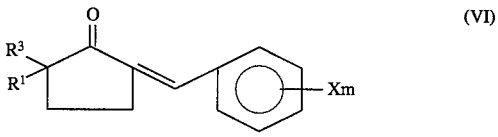

which comprises alkylating with a compound of the formula $ZR^3$ under basic conditions, wherein $R^1$ and $R^3$ individually represent a lower alkyl group; X is a halogen atom, a cyano group, an alkyl group, a haloalkyl group, a phenyl group, or a nitro group; and m is an integer of 0 to 5 (when m is 2 or larger, Xs may be either the same or different); and Z indicates a halogen atom.

5. A process for preparing a compound of the formula

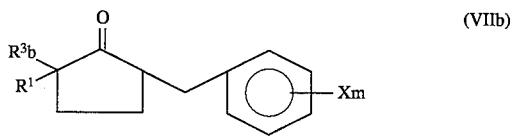

which comprises reducing a compound of the formula

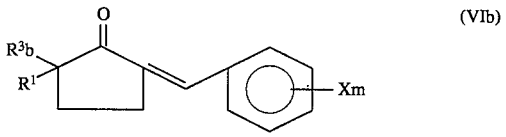

wherein $R^1$ represents a lower alkyl group; $R^3b$ is a hydrogen atom or a lower alkyl group; X is a halogen atom, a cyano group, an alkyl group, a haloalkyl group, a phenyl group, or a nitro group; and m is an integer of 0 to 5; provided when m is 2 or larger, Xs may be either the same or different.

6. An antifungal composition comprising a compound of formula (I), wherein $R^1$ and $R^2$ individually represent a lower alkyl group; X is a halogen atom, a cyano group, an alkyl group, a haloalkyl group, a phenyl group, or a nitro group; and m is an integer of 0 to 5; provided when m is 2 or larger Xs may be either the same or different.

* * * * *